United States Patent [19]

Hayashi et al.

[11] 4,256,751
[45] Mar. 17, 1981

[54] TETRAHYDROISOQUINOLINE DERIVATIVES

[75] Inventors: Kimiaki Hayashi, Suita; Jyoji Kato, Yawata; Tomofumi Uchida, Neyagawa; Naoto Yoneda, both of Suita, all of Japan

[73] Assignee: Tanabe Seiyaku Co., Ltd., Osaka, Japan

[21] Appl. No.: 92,475

[22] Filed: Nov. 8, 1979

[30] Foreign Application Priority Data

Nov. 27, 1978 [JP] Japan .................. 53/14695

[51] Int. Cl.$^3$ .................. C07D 217/16; A61K 31/47
[52] U.S. Cl. .................. 424/258; 546/146; 546/147
[58] Field of Search .................. 546/147; 424/258

[56] References Cited

U.S. PATENT DOCUMENTS 4,046,889 9/1977 Ondetti et al. .................. 424/244

FOREIGN PATENT DOCUMENTS 633216 12/1961 Canada .................. 546/147

OTHER PUBLICATIONS

Mita et al., "Chem. Pharm. Bull.," vol. 26(4), 1978, pp. 1333–1335.

*Primary Examiner*—Donald G. Daus
*Assistant Examiner*—James H. Turnipseed
*Attorney, Agent, or Firm*—Bierman & Bierman

[57] ABSTRACT

A compound of the formula:

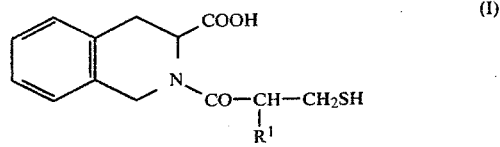

(I)

wherein $R^1$ is hydrogen or methyl, is prepared by condensing a compound of the formula:

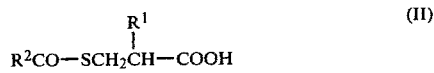

(II)

wherein $R^2$ is alkyl, aryl or aralkyl and $R^1$ is same as above, or a reactive derivative thereof with 1,2,3,4-tetrahydroisoquinoline-3-carboxylic acid or an ester thereof to give a compound of the formula:

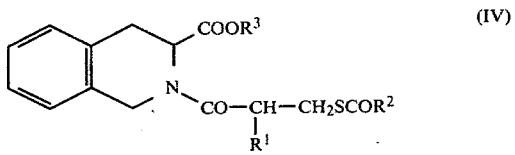

(IV)

wherein $R^3$ is an ester residue and $R^1$ and $R^2$ are same as above, followed by hydrolysis or ammonolysis of said compound (IV). The compound (I) is useful as a diagnostic or therapeutic agent for angiotensin-related hypertension.

4 Claims, No Drawings

TETRAHYDROISOQUINOLINE DERIVATIVES

This invention relates to a novel tetrahydroisoquinoline compound and a process for preparing same. More particularly, it relates to a compound of the general formula:

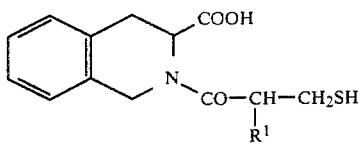

wherein R¹ is hydrogen or methyl, or a pharmaceutically acceptable salt thereof.

It is known that the action of the enzyme renin on angiotensinogen, a pseudogloblin in blood plasma, produces angiotensin I. Angiotensin I is converted by angiotensin-converting enzyme (ACE) to angiotensin II which is an active pressor substance and is causative of various forms of hypertension in mammalian species. It is also known that ACE decomposes or inactivates bradykinin, the vasodepressor substance in blood plasma, thereby serving to increase blood pressure. Thus, intensive studies have been made in recent years to investigate ACE-inhibitors because such inhibitors may prevent the formation of the pressor substance angiotensin II or the decomposition of bradykinin and be used for the treatment of patients with high blood pressure. For example, M. A. Ondetti et al. disclose that azetidine-2-carboxylic acid derivatives such as N-(3-mercapto-2-methylpropionyl)-L-proline intervene in the renin →angiotensin I→angiotensin II sequence by inhibiting angiotensin-converting enzyme and can be used in alleviating angiotensin-dependent hypertension (U.S. Pat. No. 4,046,889). I. Mita et al also disclose that (4R)-3-[(2S)-3-mercapto-2methyl-propionyl]- 4-thiazolidinecarboxylic acid is an ACE-inhibitor (Chem. Pharm. Bull. 26(1978), 1333–1335).

As a result of various investigations, we have now found that the novel tetrahydroisoquinoline compound (I) of the present invention shows potent inhibitory activity against angiotensin-converting enzyme (ACE) and is useful as a diagnostic or therapeutic agent for angiotensin-related hypertension. For example, when said inhibitory activity was estimated in vitro by the use of ACE isolated from pig's kidney, (3S)-2-[(2S)-3-mercapto-2-methyl-propionyl]-1,2,3,4-tetrahydroisoquinoline-3-carboxylic acid of the invention showed 50% inhibition of the activity of the enzyme at a concentration of about $1.5 \times 10^{-8}$ moles/liter. Moreover, the compound (I) of the present invention decreases aggregation of blood platelets and can be used to improve blood flow disturbances or other vascular diseases due to the formation of platelet aggregates (i.e., thrombus). Since the hypertensive disease is largely found in the aged subjects who show an increased tendency to capillary fragility or thrombosis, therefore, the compound (I) of the invention is useful to prevent, in addition to the treatment of hypertension, the genesis of thrombosis and other occlusive vascular diseases of such subjects. Further, the toxicity of the compound (I) is considerably low. For example, when (3S)-2-[(2S)-3-mercapto-2-methylpropionyl]-1,2,3,4-tetrahydroisoquinoline was administered orally to mice at a dose of 3 g/kg, no mouse died five days after said administration.

The compound (I) of the present invention can be used for pharmaceutical use either as the free acid or a salt thereof. Pharmaceutically acceptable salts of the compound (I) include, for example, inorganic salts such as sodium, potassium, calcium and magnesium salts, organic salts such as lysine, arginine and dicyclohexylamine salts, and the like. A daily dose of the compound (I) or a salt thereof may be about 30 mg to about 3 g, especially 50 mg to one g, per body of patients. Further, the compound (I) or a salt thereof may be used in the form of a pharmaceutical preparation containing the same compound in conjunction or admixture with a pharmaceutical excipient suitable for oral or parenteral administration. Suitable excipients include, for example, starch, lactose, glucose, potassium phosphate, corn starch, arabic gum, stearic acid and other known medicinal excipients. The pharmaceutical preparations may be in solid form such as tablets, pills or capsules; or in liquid form such as solutions, suspensions or emulsions. They may be sterilized and/or may further contain auxiliaries such as stabilizing, wetting or emulsifying agents. While the compound (I) of the present invention in which R¹ is methyl involves four optical isomers due to the two asymmetric carbon atoms, either one of said optical isomers or diastereoisomers thereof may be used for medicinal purposes. If required, a mixture of said four isomers may be used.

According to the present invention, the compound (I) can be prepared by (i) condensing a propionic acid compound of the formula:

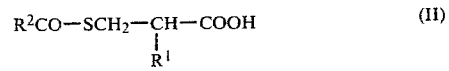

wherein R² is alkyl, aryl or aralkyl and R¹ is the same as defined above, or a reactive derivative thereof with a 1,2,3,4-tetrahydroisoquinoline-3-carboxylic acid compound of the formula:

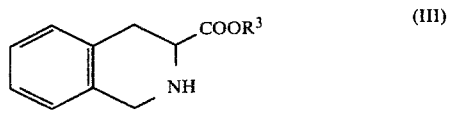

wherein R³ is hydrogen or an ester residue, to give a compound of the formula:

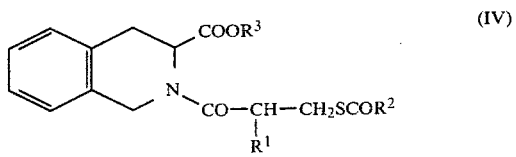

wherein R¹, R² and R³ are the same as defined above, and then (ii) hydrolyzing the compound (IV). When R³ is hydrogen, the compound (I) of the invention is also prepared by contacting the compound (IV) with ammonia.

The starting compound (III) of the invention may be obtained by a Pictet-Spengler reaction, i.e., by condensing phenylalanine and formaldehyde (Journal of The American Chemical Society 70, 180 (1948)), and if required, further esterifying the product in conventional manners. On the other hand, the starting compound (II) may be obtained by condensing an acrylic acid of the formula: $CH_2=C(R^1)\text{-}COOH$ (wherein $R^1$ is the same as defined above) with a thioic acid of the formula: $R^2COSH$ (wherein $R^2$ is the same as defined above)(-Helvetica Chimica Acta 40, 2148(1957)). In the above-mentioned formulae (II)–(IV), examples of $R^2$ includes alkyl (e.g., lower alkyl) such as methyl, ethyl, propyl; aryl such as phenyl; and aralkyl (e.g., phenyl-lower alkyl) such as benzyl. On the other hand, the ester residue shown by $R^3$ includes, for example, alkyl, (e.g., lower alkyl) such as methyl, ethyl, propyl and tert.-butyl; and aralkyl (e.g., phenyl-lower alkyl) such as benzyl. Suitable examples of the reactive derivative of the starting compound (II) includes the corresponding acid halide (e.g., chloride, bromide), mixed acid anhydrides (e.g., lower alkoxycarbonyl esters such as ethoxycarbonyl, butoxycarbonyl, isobutoxycarbonyl and amyloxycarbonyl) and active esters (e.g., esters with 1-hydroxybenzotriazole and N-hydroxysuccinimide). Among these reactive derivatives, the acid halide may be prepared by reacting the propionic acid compound (II) with thionyl chloride or thionyl bromide at 0° to 80° C., if required, in a solvent (e.g., chloroform, dichloromethane, tetrahydrofuran, dioxane, benzene). On the other hand, the mixed acid anhydride may be prepared in conventional manners, for examples, by reacting the propionic acid compound (II) with a lower alkoxycarbonyl halide (e.g., bromide, chloride) at −25° to 25° C. in the presence of an acid acceptor (e.g., triethylamine, tripropylamine, tributylamine) in a solvent (e.g., chloroform, dichloromethane, tetrahydrofuran, dioxane, benzene, cyanomethane, dimethylformamide). The active esters of the propionic acid compound (II) may be prepared by reacting said acid with 1-hydroxybenzotriazole or N-hydroxysuccinimide at −20° to 25° C. in the presence of a dehydrating agent (e.g., dicyclohexylcarbodiimide) in a solvent (e.g., tetrahydrofuran, dioxane, dichloromethane, chloroform). Further, when $R^3$ is an ester residue, the compound (III) may be employed for the condensation reaction in the form of either free base or an acid addition salt thereof. Suitable examples of said acid addition salt are hydrochloride, hydrobromide, p-tosylate and the like.

The condensation reaction of the propionic acid compound (II) (free acid) with the compound (III) can be accomplished in the presence of a dehydrating agent in a solvent. Preferred examples of said dehydrating agent include dicyclohexylcarbodiimide, N, N′-carbonyldiimidazole and the like. Tetrahydrofuran, dioxane, dichloromethane and chloroform are suitable as the reaction solvent. It is preferred to carry out the reaction at a temperature between −10° and 50° C., especially 0° and 40° C.

The condensation reaction of the reactive derivative of the propionic acid compound (II) with the compound (III) can be effected in the presence of an acid acceptor in a solvent. For example, when the compound (III) is employed in the form of free acid ($R^3=H$), said reaction is preferably carried out in the presence of an alkali carbonate (e.g., sodium carbonate, potassium carbonate) or an alkali hydroxide (sodium hydroxide, potassium hydroxide) in an aqueous solvent. Water or a mixture of water and acetone, tetrahydrofuran, dioxane or ether are suitable as the reaction solvent. On the other hand, when the compound (III) in the form of an ester ($R^3=$ester residue) is employed, said reaction is preferably carried out in the presence or absence of a trialkylamine (e.g., trimethylamine, triethylamine, tripropylamine, tributylamine), N-methylmorpholine, pyridine and so forth in a solvent. In the latter case, tetrahydrofuran, dioxane, chloroform and dichloromethane are suitable as the reaction solvent. It is preferred that the condensation reaction of the reactive derivative of the compound (II) with the compound (III) is carried out at a temperature between −10° and 60° C., especially 0° and 40° C.

The compound (I) of the invention is prepared by hydrolysis or ammonolysis of the compound (IV). The hydrolysis of the compound (IV) can be carried out in conventional manners, for example, by testing it with an alkali agent such as an alkali hydroxide (e.g., sodium hydroxide, potassium hydroxide) or alkali carbonate (e.g., sodium carbonate, potassium carbonate) or an acid such as hydrochloric acid or sulfuric acid. It is preferred to carry out said hydrolysis at a temperature between −10° and 60° C., especially 0° and 40° C. Moreover, the ammonolysis of the compound (IV) can be accomplished by treating it with ammonia in a solvent. Suitable examples of the reaction solvent include water, a mixture of water and methanol or ethanol, and the like. It is preferred to carry out said ammonolysis at a temperature between −5° and 50° C., especially 0° and 40° C. Alternatively, when the compound (IV) obtained in the preceding step is a tert.-butyl ester (i.e., $R^3=$ tert.-butyl), the compound (I) may be prepared by two steps; i.e., by treating the compound (IV) with an acid such as trifluoroacetic acid, hydrochloric acid or sulfuric acid to convert said tert.-butyl ester into the corresponding free carboxylic acid, followed by hydrolysis or ammonolysis of the resultant product under the same conditions as described above. In the latter method, the treatment of the compound (IV) ($R^3=$tert.-butyl) with trifluoroacetic acid or other acids is carried out at a temperature between −5° and 40° C. In every events, it is preferred that the hydrolysis and/or ammonolysis of the compound (IV) is carried out in an inert gas such as nitrogen or argon gas.

Since the above-mentioned reactions of the present invention are carried out without racemization, the compound (I) can be readily obtained in an optically active form by using the optically active enantiomer of the compound (III) as one of the starting materials of the invention. Further, when the compound (I) includes an asymmetric carbon atom on its side chain (i.e., when $R^3$ is methyl), the two diastereoisomers of the compound (I) may be preferably separated into each isomers by fractional recrystallization thereof.

Practical and presently-preferred embodiments of the present invention are illustratively shown in the following examples.

Experiments

ACE-inhibitory effect of the compound (I) and the preventive effect thereof upon aggregation of blood platelets were investigated by the following methods and materials.

Methods (A) ACE-inhibitory activity in vitro

50 μl of a solution containing 0.01 mole/liter of hippuryl-histidyl-leucine (substrate) and 0–100 μl of a test compound solution were added to 300 μl of a 0.2 M trishydrochloric acid buffer solution containing 0.2 mole/liter of sodium chloride. The total volume of said mixture was adjusted to 450 μl with water. Then, 50 μl of angiotensin-converting enzyme (ACE) isolated from pig's renal cortex were added to the mixture, and the mixture was allowed to stand at 37° C. for 20 minutes. The amount of histidyl-leucine produced from the substrate by the action of ACE was assayed microbiologically by the use of Leuconostoc mesenteroides P-60, and the ACE-inhibitory activity of the test compound was estimated therefrom.

(B) ACE-inhibitory activity in vivo

Normotensive rats weighing 300–400 g were anesthetized with urethane(1.5 g/kg, s.c.), and angiotensin I (300 ng/kg) was injected into the femoral vein of the rats. The pressor response to angiotensin I was measured with a pressure transducer connected to the carotid artery. Then, a test compound was injected intravenously thereto at a dose of 0.1 mg/kg, and angiotensin I (300 ng/kg) was further injected intravenously at intervals. The ACE-inhibitory activity of the test compound was estimated from the pressor responses to angiotensin I which were obtained before and after intraveous injection of the test compound.

(C) Hypotensive activity in SHR

A test compound (dose: 50 mg/kg) suspended in an aqueous carboxymethylcellulose solution was administered orally to spotaneously hypertensive rats (SHR) fasted for a day. The systolic blood pressure of the rats was measured by the tail plethysmographic technique (*The Journal of Laboratory and Clinic Medicine* 78(1971), page 957). The hypotensive activity of the test compound was estimated from the decreased level of blood pressure.

(D) Platelet aggregation-inhibiting activity

Nine volumes of blood collected from the accessary cephalic vein of male beagle dogs (body weight: 10–14 kg) were mixed with one volume of an aqueous 3.8% trisodium citrate solution, and the mixture was centrifuged at 250×g for 5 minutes to give platelet-rich plasma (PRP) as the upper layer. The bottom layer was further centrifuged at 1000×g for 15 minutes to give platelet-poor plasma (PPP) as the supernatant solution. PRP was diluted with PPP so that the blood platelet count was about 4×10⁵ cells/mm². Then, ADP was added to the diluted PRP, and the degree of ADP-induced platelet aggregation was examined by Born's method (Nature 194(1962), page 927). The solution of a test compound (100 μg/ml) was added to the diluted PRP 2 minutes before addition of ADP, and the platelet aggregation-inhibiting activity thereof was estimated in terms of the percentage inhibition of the second wave of ADP-induced platelet aggregation.

Results

The results are shown in the following tables.

TABLE 1

| Test compounds | ACE-inhibitory activity in vitro I$_{50}$(mol/liter)* | Platelet aggregation -inhibiting activity** |
|---|---|---|
| (3S)-2-[(2S)-3-mercapto-2-methyl-propionyl]-1,2,3,4-tetrahydroisoquinoline-3-carboxylic acid 2-(3-mercaptopropionyl)-1,2,3,4-tetrahydro- | 1.5 × 10$^{-8}$ | 86% |

TABLE 1-continued

| Test compounds | ACE-inhibitory activity in vitro I$_{50}$(mol/liter)* | Platelet aggregation -inhibiting activity** |
|---|---|---|
| isoquinoline-3-carboxylic salt | 8.1 × 10$^{-8}$ | 68% |

Note:
*: I$_{50}$ = a dose required to induce 50% ihibition of the ACE activity
**: percentage inhibition of the second wave of ADP-induced platelet aggregation

TABLE 2

| Test compounds | ACE-inhibitory activity in vivo* | Hypotensive activity in SHR | |
|---|---|---|---|
| | | Decrease in blood pressure | Duration of action |
| (3S)-2-[(2S)-3-mercapto-2-methyl-propionyl]-1,2,3,4-tetrahydroisoquinoline-3-carboxylic acid | 90% | ca. 20% | >6 hours |

Note:
*: percentage inhibition of ACE activity in vivo

EXAMPLE 1

(1) 5.69 g of methyl (3S)-1,2,3,4-tetrahydroisoquinoline-3-carboxylate hydrochloride are suspended in 50 ml of chloroform, and 5.6 g of triethylamine are added thereto under ice-cooling and stirring. 3-benzoylthio-2-methylpropionyl chloride (which is prepared by heating a mixture of 5.6 g of 3-benzoylthio-2-methyl-propionic acid and 6 ml of thionyl chloride at 60° C. for 2 hours, followed by distillation thereof to remove the excess of thionyl chloride) is dissolved in 10 ml of tetrahydrofuran, and said tetrahydrofuran solution is added dropwise to the suspension obtained above. After the mixture is stirred at room temperature overnight, the chloroform layer is collected therefrom and washed with water, an aqueous sodium bicarbonate solution, diluted hydrochloric acid and water, successively. The chloroform solution is dried and then distilled to remove solvent. The residue thus obtained is purified by silica gel column chromatography (Solvent, toluene-ethyl acetate (4:1)). 8.0 g of methyl (3S)-2-(3-benzoylthio-2-methylpropionyl)-1,2,3,4-tetrahydroisoquinoline-3-carboxylate are obtained as colorless oil. Yield: 80.5 %

IR$\nu_{max}^{liq.}$(cm$^{-1}$): 1740, 1660, 1640

(2) 8.0 g of methyl (3S)-2-(3-benzoylthio-2-methyl-propionyl)-1,2,3,4-tetrahydroisoquinoline-3-carboxylate are dissolved in 30 ml of methanol, and 60 ml of an aqueous 1N-sodium hydroxide solution are added thereto. The mixture is stirred at room temperature for 3 hours in nitrogen gas atmosphere. The reaction mixture is made weak-acidic with hydrochloric acid and then distilled under reduced pressure to remove methanol. The residue is extracted with ethyl acetate. The extract is washed with water, dried and distilled to remove solvent. The oily residue thus obtained is introduced into a silica gel column, and washed with ethyl acetate-chloroform (1:1) to remove benzoic acid. Then, the column is eluted with ethyl acetate-acetone (3:2). The eluate is condensed under reduced pressure, whereby 3.9 g of (3S)-2-(3-mercapto-2-methylpropionyl)-1,2,3,4-tetrahydroisoquinoline-3-carboxylic acid are obtained as colorless viscours oil. Yield: 69.8 %

(3) 3.9 g of this product and 2.5 g of dicyclohexylamine are dissolved in 30 ml of ether. n-Hexane is added to the solution, and the mixture is allowed to stand at room temperature. Crystalline precipitates are collected by filtration. Then, the precipitates obtained are recrystallized from a mixture of ethyl acetate and ether and further recrystallized from ethanol. 1.6 g of (3S)-2-[(2S)-3-mercapto-2-methylpropionyl]-1,2,3,4-tetrahydroisoquinoline-3-carboxylic acid.dicyclohexylamine salt are obtained as colorless crystals. M.p. 191°–192° C. (decomp.) (moistened at about 172° C.)

IR$\nu_{max}.^{KBr}$(cm$^{-1}$): 2500, 1630, 1560
Mass (free acid) m/e: 279 (M+)
$[\alpha]_D^{26}$ −21.0°(C=1, methanol)

Free acid (recrystallized from ethyl acetate-n-hexane):
M.p. 134°–136° C.
$[\alpha]_D^{26}$ −22.8°(C=1, methanol)

EXAMPLE 2

(1) 2.3 g of 1,2,3,4-tetrahydroisoquinoline-3-carboxylic acid are dissolved in 180 ml of water containing 3.6 g of potassium carbonate. 3-benzoylthio-propionyl chloride(prepared from 2.1 g of 3-benzoylthio-propionic acid and 4 ml of thionyl chloride) is dissolved in 15 ml of ether, and said ether solution is added dropwise to the aqueous solution obtained above. After the mixture is stirred for 3 hours under cooling, the aqueous layer is collected therefrom and is made acidic with hydrochloric acid. Said aqueous solution is extracted with ethyl acetate. The extract is washed with water, dried and then distilled to remove solvent. The residue thus obtained and 1.0 g of dicyclohexylamine are dissolved in ether. n-Hexane is added to the solution, and the mixture is allowed to stand at room temperature. Crystalline precipitates are collected by filtration. 1.5 g of 2-(3-benzoylthio-propionyl)-1,2,3,4-tetrahydroisoquinoline-3-carboxylic acid.dicyclohexylamine salt are thereby obtained. M.p. 202°–203° C.(decomp.) (This product begins to gradually decompose at 188° C.)

IR$\nu_{max}.^{nujol}$(cm$^{-1}$): 1665, 1640, 1560
Mass (free acid) m/e: 369 (M+)

(2) 1.4 g of 2-(3-benzoylthio-propionyl)-1,2,3,4-tetrahydroisoquinoline-3-carboxylic acid dicyclohexylamine salt are dissolved in 20 ml of methanol, and 20 ml of 8 % aqueous ammonia are added thereto. The mixture is stirred at room temperature overnight in nitrogen gas atmosphere. The reaction mixture is condensed to dryness under reduced pressure, and the residue is washed with ether. 0.85 g of 2-(3-mercaptopropionyl)-1,2,3,4-tetrahydroisoquinoline-3-carboxylic acid.dicyclohexylamine salt is thereby obtained. Yield: 74.7 % M.p. 193°–194° C.(decomp.) (This product begins to gradually decompose at 176° C.)

IR$\nu_{max}.^{nujol}$(cm$^{-1}$): 1635, 1560
Mass (free acid) m/e: 265 (M+)

EXAMPLE 3

(1) 3.73 g of tert.-butyl (3S)-1,2,3,4-tetrahydroisoquinoline-3-carboxylate, 3.58 g of 3-benzoylthio-2-methylpropionic acid and 2.16 g of 1-hydroxybenzotriazole are dissolved in 60 ml of tetrahydrofuran, and a solution of 3.3 g of dicyclohexylcarbodiimide in 10 ml of tetrahydrofuran is added dropwise thereto at −15° C. After said dropwise addition, the mixture is stirred at a temperature below −10° C. for 3 hours and then at room temperature overnight. Insoluble materials are removed by filtration. The filtrate is distilled under reduced pressure to remove solvent. Water is added to the residue obtained, and the aqueous mixture is extracted with ethyl acetate. The extract is washed with an aqueous 3 % citric acid solution, water, an aqueous sodium bicarbonate solution and water, sucessively. Then, the extract is dried and distilled to remove solvent. The residue thus obtained is purified by silica gel column chromatography. 5.18 g of ter.-butyl (3S)-2-(3-benzoylthio-2-methylpropionyl)-1,2,3,4-tetrahydroisoquinoline-3-carboxylate are thereby obtained as colorless oil.

Yield: 73.7 %
Mass m/e: 439 (M+)

(2) A solution of 5.18 g of tert.-butyl (3S)-2-(3-benzoylthio-2-methylpropionyl)-1,2,3,4-tetrahydroisoquinoline-3-carboxylate in 20 ml of trifluoroacetic acid is allowed to stand at room temperature for one hour. The reaction solution is distilled under reduced pressure to remove solvent. Ethyl acetate and an aqueous sodium bicarbonate solution is added to the residue. After shaking the mixture, the aqueous layer is collected therefrom and is made acidic with diluted hydrochloric acid. Then, the aqueous solution is extracted with ethyl acetate. The extract is washed with water, dried and then distilled to remove solvent. 4.4 g of (3S)-2-(3-benzoylthio-2-methylpropionyl)-1,2,3,4-tetrahydroisoquinoline-3-carboxylic acid are thereby obtained as pale yellow oil. Yield: 97.2 % 4.4 g of this product are dissolved in about 20 ml of ether, and 2.1 g of dicyclohexylamine are added thereto. Said mixture is distilled to remove ether. After the residue is washed with n-hexane, ether is added to said residue. Crystalline precipitates are collected by filtration, whereby 2.15 g of (3S)-2-[(2S)-3-benzoylthio-2-methylpropionyl]-1,2,3,4-tetrahydroisoquinoline-3-carboxylic acid.dicyclohexylamine salt are obtained as colorless crystals. Yield: 32.2 % M.p. 164°–166° C.(recrystallized from ethyl acetate-ether)

IR$\nu_{max}.^{KBr}$(cm$^{-1}$): 1665, 1630
Mass m/e(free acid): 383 (M+)
NMR(CDCl$_3$)δ(free acid): 1.1–1.5 (3H, C$\underline{H}_3$), 2.8–3.5 (5H, C$\underline{H}_2$ at 4th-position of isoquinoline skeleton,

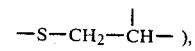

4.5–5.0(2H, C$\underline{H}_2$ at the 1st-position of isoquinoline skeleton), 5.2–5.5(1H, hydrogen atom at the 3rd-position of isoquinoline skeleton), 7.10(4H, hydrogen atoms at 5th, 6th, 7th and 8th-positions of isoquinoline skeleton), 7.25–8.10(5H, —CO—C$_6$H$_5$)

(3) 1.26 g of (3S)-2-[(2S)-3-benzoylthio-2-methylpropionyl]-1,2,3,4-tetrahydroisoquinoline-3-carboxylic acid dicyclohexylamine salt are suspended in a mixture of 15 ml of 10 % aqueous ammonia and 5 ml of methanol. The mixture is stirred at room temperature for 3.5 hours in nitrogen gas atmosphere. The reaction mixture is condensed to dryness under reduced pressure, and a mixture of ether and n-hexane is added thereto. Crystalline precipitates are collected by filtration, washed with ether and recrystallized from ethanol. 0.85 g of (3S)-2-[(2S)-3-mercapto-2-methylpropionyl]-1,2,3,4-tetrahydroisoquinoline-3-carboxylic acid.dicyclohexylamine salt is thereby obtained as colorless crystals. Yield: 82.7 % M.p. 191°–192° C.(decomp.) (This product begins to gradually decompose at about 172° C.). All the physicochemical properties of this product are identical with those of the sample obtained in Example 1-(3).

What we claim is:

1. A compound of the formula:

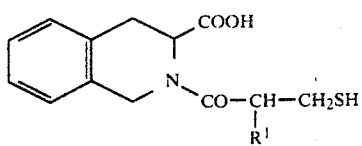 (I)

wherein $R^1$ is hydrogen or methyl, or a pharmaceutically acceptable salt thereof.

2. The compound of claim 1, in which $R^1$ is methyl.

3. The compound of claim 1, which is (3S)-2-[(2S)-3-mercapto-2-methylpropionyl]-1,2,3,4-tetrahydroisoquinoline-3-carboxylic acid or a pharmaceutically acceptable salt thereof.

4. A hypotensive composition which comprises an amount of a compound of the formula:

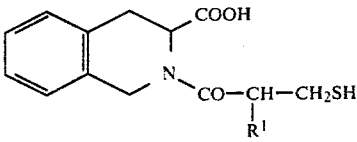

wherein $R^1$ is hydrogen or methyl, or a pharmaceutically acceptable salt thereof, and which amount is sufficient, when administered to a warm blooded animal, to provide an effective amount thereof in said animal, and a pharmaceutically acceptable carrier therefor.

* * * * *

UNITED STATES PATENT AND TRADEMARK OFFICE
CERTIFICATE OF CORRECTION

PATENT NO. : 4,256,751

DATED : March 17, 1981

INVENTOR(S) : Kimiaki Hayashi, Jyoji Kato, Tomofumi Uchida, Naoto Yoneda

It is certified that error appears in the above-identified patent and that said Letters Patent are hereby corrected as shown below:

On the first (Title) page of the patent, the reference number under Foreign Application Priority Data incorrectly appears as "53/14695" and should be corrected to --53/146951--.

Signed and Sealed this

Twenty-fifth Day of August 1981

[SEAL]

Attest:

GERALD J. MOSSINGHOFF

Attesting Officer

Commissioner of Patents and Trademarks